United States Patent [19]

Piotrowski et al.

[11] Patent Number: 4,783,564

[45] Date of Patent: Nov. 8, 1988

[54] METHOD FOR THE PREPARATION OF 1,2-DICHLOROETHANE

[75] Inventors: Bernhard Piotrowski, Lohmar; Roland Schildhauer, Niederkassel; Kurt Deselaers; Wolfgang Merkel, both of Troisdorf, all of Fed. Rep. of Germany

[73] Assignee: Huels Troisdorf AG, Troisdorf, Fed. Rep. of Germany

[21] Appl. No.: 102,291

[22] Filed: Sep. 25, 1987

Related U.S. Application Data

[63] Continuation of Ser. No. 808,010, Dec. 11, 1985, abandoned.

[30] Foreign Application Priority Data

Dec. 15, 1984 [DE] Fed. Rep. of Germany ....... 3445896

[51] Int. Cl.$^4$ ............................................. C07C 17/02
[52] U.S. Cl. ..................................... 570/254; 570/253
[58] Field of Search ........................ 570/253, 254, 258

[56] References Cited

U.S. PATENT DOCUMENTS 4,347,391 8/1982 Campbell .
4,554,392 11/1985 Leuck et al. .

FOREIGN PATENT DOCUMENTS 3146246 5/1983 Fed. Rep. of Germany .

Primary Examiner—Howard T. Mars
Attorney, Agent, or Firm—Felfe & Lynch

[57] ABSTRACT

A method is disclosed for the preparation of 1,2-dichloroethane in a reactor by the reaction of gaseous ethylene with chlorine dissolved in a hot, catalyst-containing, liquid circulating stream that is under elevated pressure and consists of chlorinated hydrocarbons. All of the chlorine is absorbed outside of the reactor, at a temperature above 90° C., a pressure of more than 4 bar, and an average residence time of less than 120 seconds. The reaction takes place at the phase boundary surface of a dispersion produced from gaseous ethylene and the chlorine-containing, liquid, circulating stream, at an energy dissipation density of 0.05 to 1000 kilowatts per cubic meter, a temperature of 90° to 200° C., and a pressure of 7 to 20 bar. Iron(III) chloride is used preferably as catalyst. Oxygen is used preferably as inhibitor for preventing the formation of byproducts. The separation of the unreacted amounts of ethylene and chlorine as well as other gaseous components from the product-containing circulating stream is performed preferably in an expansion tank.

17 Claims, 2 Drawing Sheets

1

METHOD FOR THE PREPARATION OF 1,2-DICHLOROETHANE

This application is a continuation of application Ser. No. 808,010 filed Dec. 11, 1985 now abandoned.

BACKGROUND OF THE INVENTION

The present invention is in a method for the preparation of 1,2-dichloroethane in a reactor by absorption of chlorine in a hot, catalyst-containing, liquid stream circulating under elevated pressure, which consists of chlorinated hydrocarbons, and reacting gaseous ethylene with the chlorine dissolved in the liquid phase.

The chlorination of ethylene to 1,2-dichloroethane (EDC) is an exothermic reaction in which the released reaction heat is suitable for the production of steam at the rate of about 1 ton of stea per ton of EDC (EP-OS No. 0075 742).

Different approaches are used in the known methods (U.S. Pat. No. 4,347,039) for the recovery of this reaction heat at the highest possible EDC yield, a high ethylene conversion and a high time space yield. Thus, the reaction heat is removed either in the reactor by cooling systems installed within the reactor and by evaporative cooling of the reactor content, or outside of the reactor by product cooling and evaporation. Other differences lie in the manner in which the chlorine and ethylene reactants are fed into the reaction system, the configuration of the reaction system, in the way catalysts are used to promote the desired addition reaction to EDC and of inhibitors for reducing undesired substitution reactions, such as for example the formation of 1,1,2-trichloroethane and other higher-boiling chlorinated hydrocarbons.

In particular, those methods wherein the reaction is performed above 100° C. at a pressure of more than 3 bars while the reaction system is confined in a product circuit approach having a reasonable cost of recovery of reaction heat. In such methods the release of catalyst-free product from the product circuit containing the catalyst is generally performed by flash evaporation.

As it is generally known, the efficiency of the recovery of energy, and especially the possible of producing technically useful steam, increases as the temperature level of the whole product circuit increases. On the other hand, it is also generally known that, as the temperature increases in the reactor and in the product circuit, the formation of byproducts, i.e., losses of EDC yield, due for example to substitution reactions and dehydrochlorinating cleavage of EDC, increases.

In addition to this aspect, with its corresponding influencing factors, such as catalysts and inhibitors, for example, the maximum technically achievable reaction temperature and hence also reaction pressure in ethylene chlorination is determined by the level of the chlorine input pressure. In this case the chlorine, usually coming as cell chlorine directly from a chlorine-alkali electrolysis, is fed into the reactor after compression to about 3 bar.

Directly increasing the chlorine input pressure to levels of 3 bar or more to obtain reaction temperatures of 100° C. or more is technically difficult and involves an additional costly chlorine compression. The chlorine input pressure can indirectly be increased by absorption of chlorine into EDC and, as commonly practiced in the art in the case of a liquid, raising the pressure by means of a pump. In the case of EDC, this apparently technically simple and low-cost method of chlorine absorption in the cold product stream followed by pressure increase is an unsatisfactory method of increasing the energy recovery of the reaction heat, such as for example by steam generation, or for the problem of the formation of byproducts in this process.

The important disadvantages of the formerly known application of the chlorine absorption/pressure increase method are the following:

the necessary cooling of the product circuit to temperatures lower than 40° C. in order to perform the desired chlorine absorption, and the subsequent heating of the chlorine-containing EDC, necessitate a considerable expenditure of energy;

due to the relatively high chlorine concentration in the EDC, of more than 8% by weight, as a result of the chlorine absorption process, it is impossible to avoid—even despite the use of inhibitors such as oxygen—the undesirable formation of byproducts, especially due to substitution reactions, on account of the need to raise the temperature of this solution to close to the reaction temperature, and the long residence time which this entails between the chlorine absorption and the start of the reaction in the reactor.

This heretofore unsatisfactory application of the chlorine absorption/pressure increase method has another disadvantageous effect. When this chlorine-containing EDC solution is heated to virtually the reaction temperature on outgassing of the chlorine from the EDC is unavoidable. A two-phase flow forms with elevated temperature and a high chlorine concentration at the phase boundary. This promotes the above-mentioned secondary reactions.

The measures disclosed heretofore for the reduction of secondary reactions at a reaction temperature above 100° C. are based largely on fluid-dynamic controlling factors in addition to the advantageous use of appropriate catalysts and inhibitors in the reaction system. For example, the attempt has been made by means of a very fine and very uniform distribution of the reactants to prevent irregularities of concentration and temperatures such as can occur for example, when chlorine and ethylene bubbles meet. These include efforts to forestall contact between the gaseous reactants chlorine and ethylene, by having the chlorine dissolve preferentially in EDC and bringing this solution into a reaction with the gaseous, very finely divided ethylene.

U.S. Pat. No. 4,554,392 has recourse to this control of the reaction through the phase boundary. To do this, a reactor is selected in both cases which has the typical characteristics of a loop reactor, such as, for example, the feeding of product into the bottom part of the reactor with the flow configuration characteristic thereof, namely upward in the central inside tube and downward in the outer part, and a sufficiently great rate of circulation of the flow of, for example, 30 to 200 kilograms per square meter per second, or a velocity greater than 0.1 meter per second in the mixing zone of the inner tube.

The examples of these methods which are herein given achieve only partially their aim of controlling the reaction at the phase boundary. For example, in these embodiments of the reactor the fine distribution of the ethylene bubbles is accomplished preferentially in a nozzle provided for the purpose at the bottom of the reactor and in the inside tube of the loop reactor. In spite of the stated rates of circulation, it is not possible to avoid completely the escape of the ethylene bubbles from the reactive phase boundary of the liquid reaction phase containing catalyst and chlorine into the gas phase above it which consists of EDC in vapor form, unreacted materials, such as chlorine and especially ethylene, as well as other inert gaseous components. Especially in the case of a boiling reactor, the formation of vapor bubbles in the upper part of the liquid reaction phase causes the ethylene bubbles therein to be carried over to a greater extent and thus to be withdrawn from the desired reaction at the phase boundary surface.

The present invention is addressed to a method wherein chlorine is absorbed at a high temperature with a minimum formation of byproducts, without having to perform the above-described, disadvantageous cooling followed by heating of the product stream. A further object of the invention is to prevent any separation into a disperse gas-liquid phase and the gaseous phase situated above it at the phase boundary.

SUMMARY OF THE INVENTION

These problems are solved by the present invention. The present invention is a method for the preparation of 1,2-dichloroethane in a reactor by absorption of chlorine in a hot, catalyst-containing, liquid stream circulating under elevated pressure, which consists of chlorinated hydrocarbons, and reacting gaseous ethylene with the chlorine dissolved in the liquid phase, introducing the solution and gaseous ethylene into the reactor to produce a dispersion having a phase boundary surface, at an energy dissipation density of 0.05 to 1000 kilowatts per cubic meter at a temperature of 90° to 200° C. and a pressure of 7 to 20 bars wherein reaction between ethylene and chlorine takes place to form the 1,2-dichloroethane; and separating the 1,2-dichloroethane from a circulating stream from the reactor.

It has been found that, in the chlorine absorption and the subsequent transport or storage of a solution of chlorine in EDC at elevated temperature, certain conditions must be maintained in order to minimize the undesired formation of byproducts. For example, it is advantageous in the chlorine absorption and in the transport of the EDC-chlorine solution at 100° C. in the stream circulating between the point of introduction of the gaseous chlorine and the reactor to maintain a chlorine concentration of less than 3 percent by weight. Furthermore, an average residence time of less than 120 seconds should be maintained in the circulating stream from the injection of the chlorine for absorption to the beginning of the reaction with ethylene. Furthermore, the additional use of inhibitors to prevent the formation of byproducts is advantageous. For example, the addition of oxygen inhibits substitution reactions, i.e., the formation of 1,1,2-trichloroethane and other, higher-boiling chlorinated hydrocarbons. It has been found advantageous to use as an inhibitor oxygen or a gas containing oxygen, in the amount of 0.05 to 0.3 percent by weight, reckoned as molecular oxygen, with respect to the amount of chlorine put into the reaction.

Other known inhibitors, such as cresols for example, can be used in the method of the invention, either alone or in combination with oxygen.

In the method of the invention, known catalysts for the reaction between chlorine and ethylene to form 1,2-dichloroethane can be used.

Known catalysts are Lewis acids, iron(III) chloride, anhydrous tetrachloro ferrates (1−) and such substances that can generate tetrachloro ferrates (1−) from a reaction mixture.

Especially the use of iron(III) chloride or a compound containing iron(III) chloride as a catalyst has been found advantageous. When the reaction system is filled with EDC, the catalyst is added through a dissolving tank. Preferably it is contained in the circulating stram in the amount of 30 to 3000 ppm by weight, reckoned as ferric trichloride.

To achieve the limited residence time of the chlorine during its absorption, as required by the method of the invention, substance-exchange apparatus having a specific exchange surface area of at least 1000 square meters per cubic meter, such as, for example, jet washers, are especially suitable.

Another contribution to the solution of the problem to which the invention is addressed consists of the knowledge that, for the yield as well as the temperature and concentration program of the reaction, i.e., also for its selectivity at relatively high temperatures, a suitable energy dissipation density must prevail in the reactor, namely, one of 0.05 to 1000 kilowatts per cubic meter, at the phase boundary surface of the dispersion produced from gaseous ethylene and the circulating liquid containing chlorine. The energy dissipation density of this magnitude is necessary because the specific surface area of the ethylene bubbles is uniformly distributed in the method according to the invention.

The energy dissipation density of the magnitude in accordance with the invention counteracts the tendency of the fine ethylene bubbles to combine to form large bubbles when the ethylene is introduced into the reactor, and thus it contributes to making a large specific surface area of ethylene available for the reaction. Furthermore, the energy dissipation density according to the invention prevents the phase separation—caused by the coalescence of the ethylene bubbles in the reactor—into a gaseous phase in the upper part and a heterogeneous gas-liquid phase in the lower part of the reactor.

As soon as the gaseous ethylene is dispersed in the circulating liquid containing chlorine, the energy dissipation density according to the invention is produced and maintained by a device suitable for this purpose, such as a static mixer or a jet nozzle, for example. It has also proven advantageous to introduce any inhibitors that are to be used in the mixing zone of the reactor and there to distribute them with an energy dissipation density of 10 to 1000 kW per cubic meter. Surprisingly, it has furthermore been found that the coalescing tendency described above can be reduced, i.e., that the ethylene bubbles remain stable for a longer time under comparable fluid-dynamic conditions, if the concentration of the dissolved chlorine in the circulating stream amounts to at least 100 ppm by weight at the exit from the reactor.

In the above-mentioned dispersion of the ethylene in, for example, a static mixer, the latter simultaneously serves as a reaction zone, i.e., a substantial part of the ethylene and chlorine reactants right in the mixing apparatus to form 1,2-dichloroethane.

Then the highly disperse reaction phase is fed into a central pulse-exchange tube situated in the reactor, such that an energy dissipation density of 0.05 to 100 kW per cubic meter is established in the tube flow and in the outer margin of the tube. This gas-liquid dispersion, thus set in motion, leaves the reactor after a reversal of direction in the bottom part, without permitting phase separation in the reactor. At the same time, at an average residence time of less than 60 minutes, the by far greatest part of the ethylene has reacted with the chlorine to form EDC. The still unreacted part of the ethylene in the remaining gas bubbles can be separated from the catalyst-containing circulating stream together with the gaseous EDC that has formed, in an expansion vessel connected to the output of the reactor. The recovery of the gaseous EDC from the other gaseous components is performed in condensers by cooling with water and/or brine. While the catalyst-free EDC is being fed possibly to further processing operations, the gaseous components still remaining are fed, if desired, to a post-reaction or directly to an exhaust gas processor.

In addition to the energy recovery by condensation of the gaseous EDC from the expansion vessel, in the method of the invention the greatest part of the reaction heat is taken directly from the liquid, catalyst-containing EDC circulating stream by suitable heat exchangers and used for steam generation and for heating the bottom of distillation columns.

Another especially advantageous embodiment of the invention for the recovery of energy from the EDC circuit is based on the additional compression of gaseous EDC in which a portion amounting up to a multiple of the produced EDC from the circuit 18 is evaporated in an additional expansion vessel 12a, then raised to a higher temperature compression, and is cooled, e.g., by the production of steam, and condensed. In this case it has been surprisingly found that a heat treatment of EDC at 165° C. and the corresponding vapor pressure, for a period of 30 minutes, did not result in any undesired formation of byproduct.

The liquid, catalyst-containing EDC circulating stream is recycled to the chlorine absorption.

The various features of novelty which characterize the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

DESCRIPTION OF PREFERRED EMBODIMENTS

Figure 1:
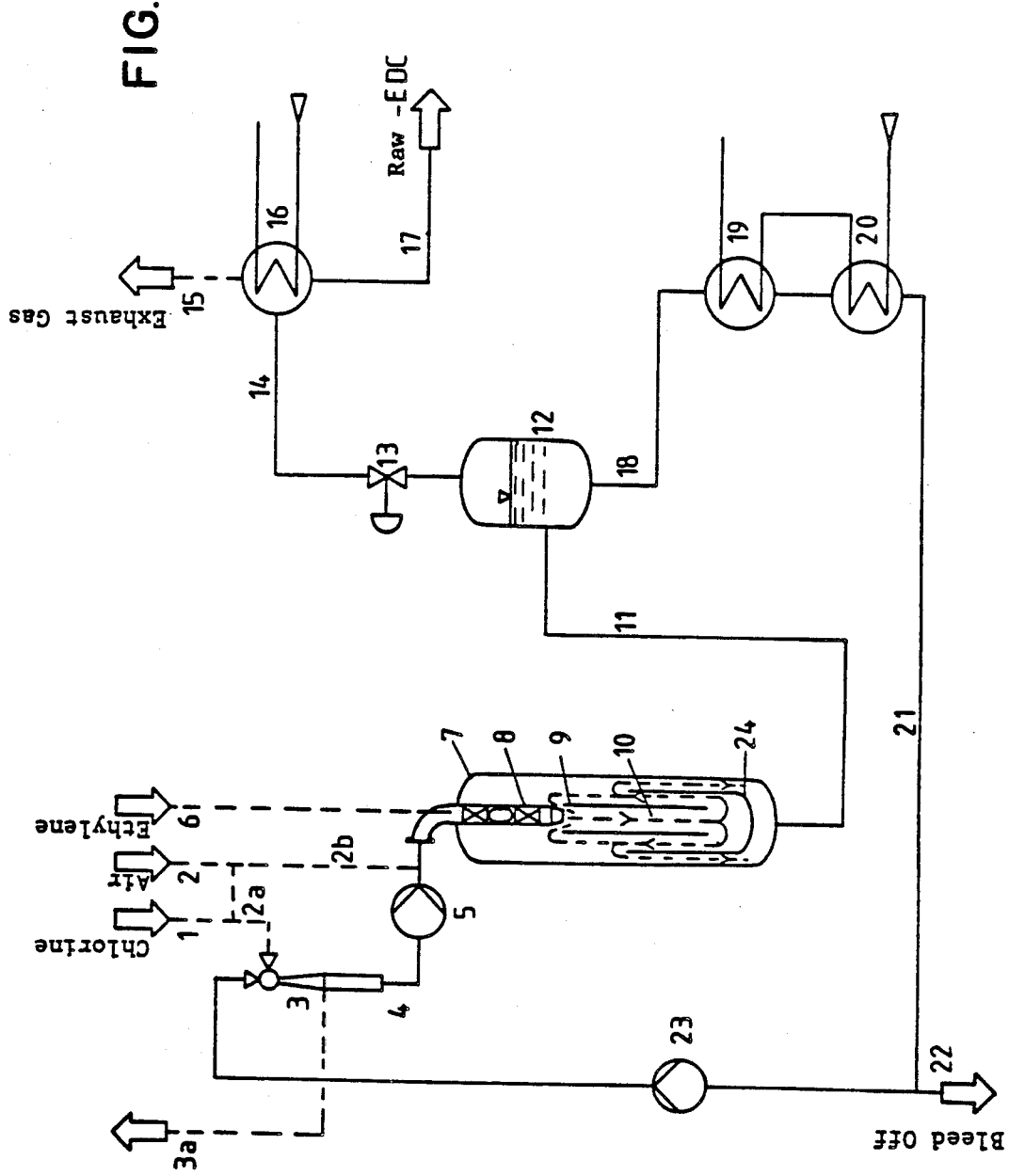
FIG. 1 is a flow diagram.

Referring to FIG. 1, chlorine gas 1, from a chlorine-alkali electrolysis for example, containing an inter gas content of up to 10% by volume consisting essentially of nitrogen, hydrogen and carbon dioxide, and having a pressure of about 3.2 bar, is mixed with air at 2a. The air-chlorine gas mixture is then contacted in a liquid jet washer 3, under a pressure of at least 4 bar, with a circulating stream 21. Stream 21 consists essentially of EDC at a temperature of more than 90° C. containing more than 30 ppm by weight of catalyst. Stram 21 is raised by the pump 23 to a driving jet pressure of at least 5 bar, such that the requirements explained above for the chlorine absorption (substance exchange at a specific exchange surface area of at least 1000 square meters per cubic meter and an average residence time from the addition of chlorine to the washer 3 to the beginning of the reaction with ethylene in the static mixer 8 of less than 120 seconds) are satisfied. Especially if the inert gas content in the electrolytic chlorine is high, the inert gases which are dissolved in the EDC or in the circulating stream can be carried off through the line 3a in the upper part of the washer 3. The EDC circuit stream 4, containing less than 3% chlorine by weight, is pressurized by pump 5 to about 2.5 bars above the prevailing reactor pressure whih is more than 6 bar. The preferred reactor pressure range is 7 to 20 bar. The pressurizing of stream 4 results in an energy dissipation density of at least 0.05 kW per cubic meter in the static mixer 8 and in the pulse exchange tube 9, and will serve to establish the circulating stream 10 in the reactor 7. With a comparably high input pressure as in the case of stream 4 at the reactor entrance, a mass of ethylene virtually equivalent to the chlorine is introduced through the static mixer 8 into the reactor 7 such that a low chlorine concentration of 100 to about 300 ppm by weight is established in the EDC circuit 11 at the reactor outlet.

It has proven to be especially advantageous to introduce air acting as an inhibitor into the circulating stream 4 before the chlorine and ethylene reactants enter the static mixer 8 where they are homogenized. The reaction takes place at a temperature of 90° to 200° C., preferably 120° to 160° C., a pressure of 7 to 20 bars, and an energy dissipation density of 0.5 to 1000 kW per cubic meter. This energy dissipation density is calculated from the pressure drop and the volume flow rate of the liquid phase flowing through the static mixer 8 up to the outlet of the reactor 7. The velocity in the liquid phase amounts to at least 0.5 m/sec. This velocity prevails in the circulating stream 10 up to the outlet of the reactor 7. The velocity of the liquid phase equals or is larger than the upward velocity of the bubbles so that a phase separation is avoided. By means of the internal tube 9 and the reversal 24, the circulating stream 10 is produced.

The virtually fully reacted reaction mixture leaves reactor 7, after an average residence time of the ethylene, from its entry into the reactor 7 to the phase separation in the expansion vessel 12, of less than 60 minutes, preferably 2 to 60 minutes, in the form of a gas-liquid dispersion 11, and is introduced into the expansion vessel 12.

Figure 2:
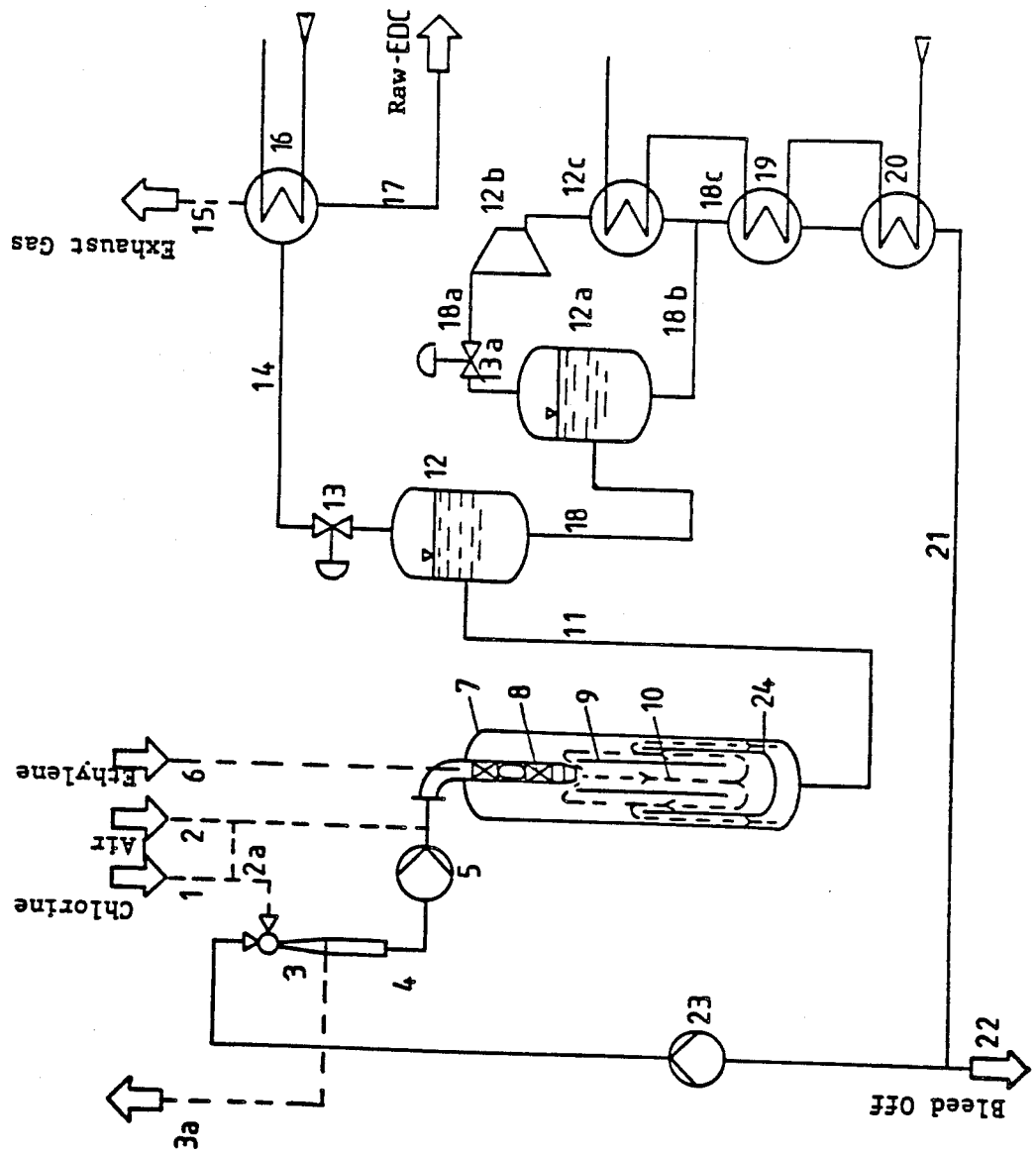
FIG. 2 is a flow diagram schematically showing additional energy recovery.

A phase separation into a gaseous phase and a liquid phase takes place in a vessel 12. The gaseous phases consists of inert-gas contents of the raw materials and of the inhibitors, unreacted chlorine and ethylene, volatile reaction products and EDC vapors, which are in equilibrium with the substances named above under the process conditions here involved. The liquid phase consists of EDC containing catalyst plus small amounts of dissolved reactants. The chlorine concentration in the circulating stream 11 amounts preferably to 100 to 200 ppm by weight when it emerges from the reactor 7. By means of the expansion valve 13, the pressure in the expansion tank is reduced such that, under the conditions specified above, just as much EDC is evaporated as is formed in the reactor 7. The separation of the gaseous EDC from gas stream 14 into exhaust gas stream 15 and the raw EDC stream 17 is performed, for example, by a single or multiple direct or indirect condensation. In FIGS. 1 and 2, the condensation is performed, for example, in the single, indirect form in heat exchanger 16.

In addition to the objective of energy recovery, there is the matter of exhaust gas treatment and the processing of the raw EDC, which are important in the separation of the raw EDC from the gas stream 14. The circulating liquid EDC 18, only slightly cooled by the EDC evaporation in vessel 12, is fed to an energy recovery stage, such as a steam recovery system or to a system for heating the bottom of a still. This stage can consist, for example, of a plurality of suitable heat exchangers 19 and 20 (see FIG. 1).

In an especially advantageous embodiment of the process, as shown in FIG. 2, a portion up to a multiple of the produced EDC is evaporated from the circulating stream 18 in an additional expansion vessel 12a, raised to a higher temperature by compression in a compressor 12b, then cooled and condensed in the heat exchanger 12c, e.g., by the production of steam. Then steam will form at a higher pressure in the heat exchanger 12c than corresponds to the temperature at the outlet of the EDC circulating stream 11 from the reactor 7. The circulating EDC stream 18c is heated by the heat exchangers 19 and 20 preferably to such a temperature that up to 3% of chlorine, by weight, is absorbed in the washer 3.

An intermittent release of a partial amount 22 from the circulating stream 21 is necessary whenever the content of 1,1,2-trichloroethane and other higher-boiling chlorinated hydrocarbons is equal to or greater than 1% by weight and an iron(III) chloride catalyst concentration of 2000 ppm by weight is exceeded.

EXAMPLE 1 (FIG. 1)

The apparatus represented diagrammatically in FIG. 1 was filled with 2200 kg of high-purity ethylene dichloride (EDC). In this circulating mass, 1000 mg of iron-(III) chloride per kilogram of EDC had already been dissolved as catalyst. The pH of the catalyst solution was 2.4.

For the chlorine absorption in the liquid jet washer 3, 400 kg/h of electrolytic chlorine 1 with an inert gas content of 5% by volume and 2 kg/h of air 2 were introduced together into the suction line of the washer through the line 2a, and dissolved within about 50 seconds in a stream of EDC circulating at 22 t/h at a temperature of 99° C. and a pressure in the washer of 5 bar. The circulating stream served as a driving jet and for this purpose had to be raised by the pump 23 to an input pressure of 7.5 bar. The chlorine-containing circulating stream 4 was raised by pump 5 to a pressure of 10 bar, and 1 kg/h of air was added to it through line 2b before entry into the reactor 7. To this chlorine-containing circulating stream approximately 153 kg/h of ethylene pressurized to 11 bar were introduced through the static mixer 8 into the reactor 7 which was completely filled with EDC. By a fine regulation of the ethylene stream 6, the chlorine concentration in the EDC circuit 11 was adjusted to approximately 200 ppm by weight. The reaction of the chlorination of ethylene to EDC, taking place in a gas/liquid dispersion, for a reactor capacity of 1.1 cubic meter, an energy dissipation density in the reactor of approximately 1 kW per cubic meter, and a reaction pressure of 8 bar, resulted in a temperature of 132° C. at the outlet from the reactor.

At this temperature the almost completely reacted circulating stream 11 enters the expansion tank 12. By means of a level control an amount of EDC is vaporized with the gaseous components through the pressiure release valve 13 such that a constant level is produced in the expansion tank. The amount of heat that is released upon the separation of the raw EDC 17 from the exhaust gas 15 by condensation in the heat exchanger 16 was used, for example, for preheating boiler feed water.

The circulating stram 18, cooled to about 128° C., is cooled in the heat exchangers 19 and 20 to 99° C., producing 450 kg/h of a saturated steam at 118° C. and 1.8 bar.

An evaluation showed the following results:
Conversion of ethylene: 99.6%
conversion, ethylene to EDC: 98.9%
resulting in a yield of: 98.5%
of the theory.

EXAMPLE 2

In contrast to Example 1, with a comparable experimental set-up, the mass stream of the reactant chlorine 1 was reduced to 200 kg/h and that of the ethylene 6 was reduced to 77 kg/h, and the flow of the air at 2a and 2b was reduced by one-half.

Under otherwise the same reaction conditions, such as the charge of 2200 kg, the catalyst concentration of 1000 ppm by weight, the EDC stream circulating at 22 metric tons of EDC per hour, and the same pressures as in Example 1, the temperature in the EDC stream 21 was raised from the former 99° C. to 120° C. Under these absorption and reaction conditions, a temperature of 135° C. established itself at the outlet from the reactor.

After the separation of the product EDC in the expansion tank 12 by evaporation, a temperature established itself in the EDC stream 18 of 133° C. The stream 21, cooled to 120° C. in the heat exchangers 19 and 20, was used for the production of 220 kg/h of saturated steam at a temperature of 122° C. and a pressure of about 2 bar.

Evaluation gave the following results:
Conversion of ethylene: 99.9%
conversion, ethylene to EDC: 99.3%
resulting in a yield of: 99.2%
of the theory.

EXAMPLE 3 (FIG. 2)

The experiment performed in Example 3 under the same conditions as in Example 2 differs in that about 1.5 t/h of EDC 18a from the EDC stream 18 flowing at 22 t/h was vaporized through the relief valve 13a in the expansion tank 12a and fed to the vapor compressor 12b. The EDC vapor was compressed to a pressure of 5.8 bar and left the compressor with a temperature of about 150° C., and was then condensed in the heat exchanger 12c and combined with the catalyst-containing stream 18b. This circulating stream 18c passed, as previously described, through the heat exchangers 19 and 20. The saturated steam thus produced had a pressure of 3 bar, about 1 bar higher than in the case of Example 2.

The ethylene conversion and the EDC yield were not affected by this, and corresponded to the data given in Example 2.

EXAMPLE 4

In an experiment similar to Example 2, the circulating stream 21 was again reduced by one-half, and the average residence time in the chlorine absorption and in the reactor was increased at chlorine concentrations comparable to Example 1. An evaluation was made taking into account a corresponding reduction of the energy dissipation density to about half of that selected in Examples 1 to 3, at temperatures in the chlorine absorption in washer 3 and at the output of the reactor similar to those in Example 1, and the results were as follows:
Conversion of ethylene: 99.4% conversion of ethylene to EDC: 98.0%
resulting in a yield of: 97.4%
of the theory.

It will be understood that the specification and examples are illustrative but not limitative of the present invention and that other embodiments within the spirit and scope of the invention will suggest themselves to those skilled in the art.

We claim:

1. A method for the preparation of 1,2-dichloroethane comprising:
    absorbing chlorine, at a temperature above 90° C., a pressure greater than 4 bars and at an average residence time of less than 120 seconds, in a circulating hot pressurized liquid stream to form a solution containing less than 3% chlorine by weight, said stream consisting of chlorinated hydrocarbons and a catalyst of a metal chloride or a metal chloride containing compound;
    pressurizing said solution to a pressure of about 2.5 bars above the pressure of a reactor; said reactor being operated at a pressure of 7 to 20 bars;
    introducing the solution and gaseous ethylene into the reactor to produce a dispersion having a phase boundary surface, at an energy dissipation density of 0.05 to 1000 kilowatts per cubic meter at a temperature of 90° to 200° C. wherein reaction between ethylene and chlorine takes place in a mixing zone in said reactor to form the 1,2-dichloroethane; and
    separating the 1,2-dichloroethane from a circulating stream from the reactor.

2. The method of claim 1, wherein unreacted gaseous components leave the reactor in the circulating stream.

3. The method of claim 2, wherein the circulating stream contains at least 100 ppm by weight of chlorine.

4. The method according to claim 1, wherein the reaction between ethylene and chlorine takes place at a temperature of 120° to 160° C.

5. The method according to claim 1, wherein the catalyst is iron(III) chloride or a compound containing iron(III) chloride and is contained in the pressurized stream in an amount of 30 to 3000 ppm by weight, calculated as $FeCl_3$.

6. The method according to claim 1, wherein at least one inhibitor is present to prevent the formation of byproducts in the reaction between ethylene and chlorine.

7. The method according to claim 6, wherein said least one inhibitor is selected from the group consisting of oxygen or a gas containing oxygen and is used in a proportion of 0.05-0.3 wt.-%, reckoned as $O_2$, with respect to the amount of chlorine used for the reaction.

8. The method according to claim 6, wherein said least one inhibitor is introduced into the mixing zone of the reactor and distributed with an energy dissipation density of 10 to 1000 $kW/m^3$.

9. The method of claim 6, wherein components of the at least one inhibitor and of the chlorine gas which are not soluble in the pressurized stream are removed before entry into a reaction zone of the reactor.

10. The method of claim 1, wherein the 1,2-dichloroethane is separated from the circulating stream in an expansion tank and the ethylene has an average residence time from its introduction into the reactor until separation in the expansion tank of less than 60 minutes.

11. The method according to claim 1, wherein the circulating stream from the reactor has a chlorine concentration of 100 to 200 ppm by weight.

12. The method according to claim 4, wherein the unreacted amounts of ethylene and chlorine are separated from the circulating stream in the expansion tank.

13. The method according to claim 12, wherein the undissolved components of the inhibitors are separated from the circulating stream in the expansion tank.

14. The method according to claim 12, wherein the input chlorine gas as well as easily volatile reaction products are separated from the circulating stream in the expansion tank.

15. The method of claim 1, wherein the 1,2-dichloroethane is separated from the circulating stream in an expansion tank and a second circulating stream exits said tank and is cooled with at least one heat exchanger to produce steam.

16. The method of claim 1, wherein the 1,2-dichloroethane is separated from the circulating stream in an expansion tank and a second circulating stream exits said tank and is cooled by heat exchange means to preheat water.

17. The method of claim 15, wherein a portion, up to a multiple of the produced 1,2dichloroethane is evaporated from the second circulating stream in a second expansion tank, then brought to a higher temperature by compression, and cooled and condensed, by the production of steam.

* * * * *